United States Patent [19]

Rovnyak et al.

[11] Patent Number: 5,143,915

[45] Date of Patent: Sep. 1, 1992

[54] DIHYDROPYRIMIDINE MACROCYCLIC LACTONES USEFUL AS CALCIUM ANTAGONISTS AND AGONISTS

[75] Inventors: George C. Rovnyak, Hopewell; Spencer D. Kimball, East Windsor, both of N.J.

[73] Assignee: E. R. Squibb & Sons, Inc., Princeton, N.J.

[21] Appl. No.: 558,266

[22] Filed: Jul. 25, 1990

[51] Int. Cl.$^5$ .................. A61K 31/55; A61K 31/505; A61K 31/535; C07D 497/04

[52] U.S. Cl. .................. 514/212; 514/228.5; 514/232.8; 514/267; 540/600; 544/60; 544/115; 544/229; 544/250; 544/311; 556/418; 556/427; 568/62; 568/65; 568/424; 568/705

[58] Field of Search ............... 540/600, 1; 544/60, 544/115, 250; 514/212, 228.5, 232.8, 267

[56] References Cited

U.S. PATENT DOCUMENTS 4,728,652  3/1988  Atwal ........................... 514/274

OTHER PUBLICATIONS

Rovnyak, G. et al., "Studies Directed Toward Ascertaining the Active Conformation of 1,4-Dihydropyridine Calcium Entry Blockers", Journal of Medicinal Chemistry, (1988), 936-944.

Seidel, W. et al., "Rigid Calcium Antagonists of the Nifedipine-Type: Geometric Requirements for the Dihydropyridine Receptor", QSAR Strategies Des. Bioact. Compd., Proc. Eur. Symp. Quant. Struct-Act. Relat., 5th, [54QWAZ], 1984, (Pub. 1985), 366-369 (Eng.).

*Primary Examiner*—Mukund J. Shah
*Assistant Examiner*—E. Bernhardt
*Attorney, Agent, or Firm*—Timothy J. Gaul

[57] ABSTRACT

A compound of the formula

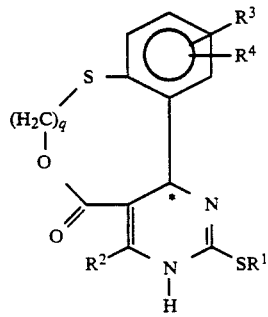

(symbols defined in the specification), its 3,4-dihydropyrimidine tautomer form and pharmaceutically acceptable salts thereof have calcium entry blocking activity. A process of preparation, pharmaceutical composition and method of using the compound to reduce blood pressure are also provided.

10 Claims, No Drawings

DIHYDROPYRIMIDINE MACROCYCLIC LACTONES USEFUL AS CALCIUM ANTAGONISTS AND AGONISTS

FIELD OF THE INVENTION

This invention relates to dihydropyrimidine macrocyclic lactones and to compositions and methods of use for such compounds as cardiovascular agents.

BRIEF DESCRIPTION OF THE INVENTION

A compound of the formula

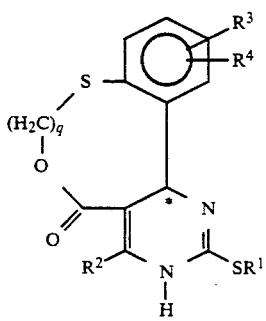

its 3,4-dihydropyrimidine tautomer form and the pharmaceutically acceptable salts thereof have been found to possess activity as calcium antagonists and as calcium agonists, making them useful as cardiovascular agents. In formula I and throughout this specification, the above symbols are as defined below:

$R^1$ is lower alkyl, lower alkenyl, lower alkynyl, —$(CH_2)_m$-cycloalkyl, —$(CH_2)_m$-aryl, —$(CH_2)_n$-heterocyclo, —$(CH_2)_p$—OH, —$(CH_2)_p$—O-lower alkyl, —$(CH_2)_p$—O—$(CH_2)_m$-aryl, —$(CH_2)_p$—SH, —$(CH_2)_p$—S-lower alkyl, —$(CH_2)_p$—S—$(CH_2)_m$-aryl,

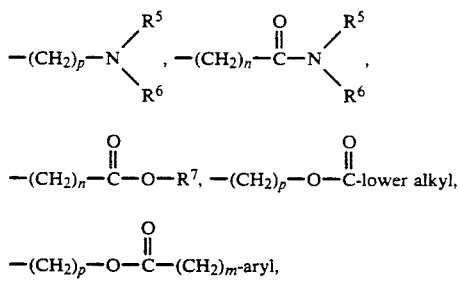

or halo-substituted lower alkyl, $R^2$ is hydrogen, lower alkyl, lower alkenyl, lower alkynyl, —$(CH_2)_m$-cycloalkyl, —$(CH_2)_m$-aryl, —$(CH_2)_n$-heterocyclo, —$(CH_2)_n$—OH, —$(CH_2)_n$—O-lower alkyl, —$(CH_2)_n$—O—$(CH_2)_m$-aryl, —$(CH_2)_n$—SH, —$(CH_2)_n$—S-lower alkyl, —$(CH_2)_n$—S—$(CH_2)_m$-aryl,

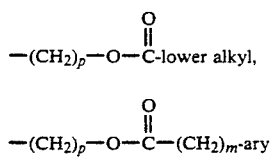

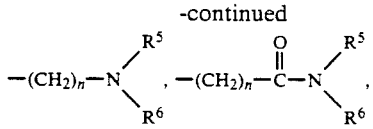

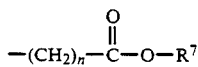

or halo-substituted lower alkyl;

one of $R^3$ and $R^4$ is hydrogen and the other is lower alkyl of 1 to 4 carbons, lower alkylthio of 1 to 4 carbons, lower alkoxy of 1 to 4 carbons, halo, nitro, cyano, hydroxy, amino, —N—H-alkyl wherein alkyl is of 1 to 4 carbons, —N(alkyl)$_2$ wherein alkyl is of 1 to 4 carbons, $CF_3$, NCS, $OCHF_2$,

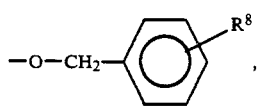

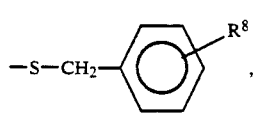

—O—$CH_2$-cycloalkyl, or —S—$CH_2$-cycloalkyl; or $R^3$ and $R^4$ are each independently methyl, methoxy, methylthio, halo, $CF_3$, nitro, amino, or $OCHF_2$;

$R^5$ and $R^6$ are independently selected from the group consisting of hydrogen, lower alkyl, and —$(CH_2)_m$-aryl or $R^5$ and $R^6$ together with the N atom to which they are attached complete a heterocyclic ring of the formula

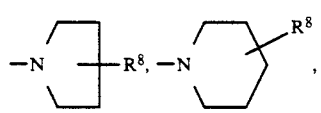

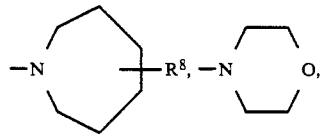

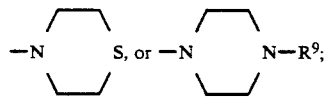

$R^7$ is hydrogen, lower alkyl, —$(CH_2)_m$-aryl, or a pharmaceutically acceptable salt forming ion;

$R^8$ is hydrogen, lower alkyl of 1 to 4 carbons, lower alkoxy of 1 to 4 carbons, lower alkylthio of 1 to 4 carbons, halo, hydroxy, or $CF_3$;

$R^9$ is hydrogen, lower alkyl of 1 to 4 carbons,

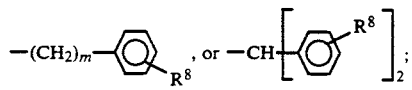

m is zero or an integer from 1 to 6;
n is an integer from 1 to 6;

p is an integer from 2 to 6; and
q is an integer from 3 to 8.
The asterisk (*) denotes an asymmetric carbon.
Preferred compounds of formula I are those wherein:
$R^1$ is methyl;
$R^2$ is methyl;
one of $R^3$ and $R^4$ is hydrogen and the other is nitro; and
q is 5.

Novel intermediates and a novel process for preparing compound I is also provided.

DETAILED DESCRIPTION OF THE INVENTION

Definition of Terms

The term "lower alkyl" used in defining various symbols refers to straight or branched chain saturated hydrocarbon radicals having up to eight carbons, preferably from one to five carbons. Similarly, the terms "lower alkoxy" and "lower alkylthio" refer to such lower alkyl groups attached to an oxygen or sulfur.

The term "lower alkenyl" refers to straight or branched chain hydrocarbon radicals having from two to eight carbons and one double bond, preferably three to five carbons. The term "lower alkynyl" refers to straight or branched chain hydrocarbon radicals having from two to eight carbons and one triple bond, preferably three to five carbons.

The term "cycloalkyl" refers to saturated carbocyclic rings of 4 to 7 carbon atoms with cyclopentyl and cylohexyl being most preferred.

The term "halo" refers to chloro, bromo and fluoro.

The term "halo-substituted lower alkyl" refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —N—H-alkyl wherein alkyl is of 1 to 4 carbons, —N(alkyl)$_2$ wherein alkyl is of 1 to 4 carbons, $CF_3$, NCS, $OCHF_2$,

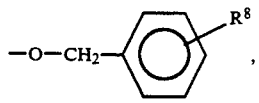

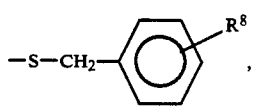

—O—CH$_2$-cycloalkyl, or —S—CH$_2$-cycloalkyl, and di-substituted phenyl, 1-naphthyl, or 2-naphthyl wherein said substituents are selected from methyl, methoxy, methylthio, halo, $CF_3$, nitro, amino, and $OCHF_2$.

The term "heterocyclo" refers to fully saturated or unsaturated rings of 5 or 6 atoms containing one to four N atoms, or one O atom, or one S atom, or one O atom and one or two N atoms, or one S atom and one or two N atoms. The heterocyclo ring is attached by way of an available carbon atom. Preferred monocyclic heterocyclo groups include 2- and 3-thienyl, 2- and 3-furyl, 2-, 3- and 4-pyridyl, and imidazolyl. The 2-, 3-and 4-pyridyl may also have a substituent selected from lower alkyl of 1 to 4 carbons, lower alkoxy of 1 to 4 carbons, and lower alkylthio of 1 to 4 carbons on an available carbon. The term "heterocyclo" also includes bicyclic rings wherein the five or six membered ring containing O, S and N atoms as defined above is fused to a benzene ring and the bicyclic ring is attached by way of an available carbon atom in the benzene ring. Preferred bicyclic heterocyclo groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

Process of Preparation

Compounds of formula I can be prepared by the following exemplary process.

The known compound of the formula

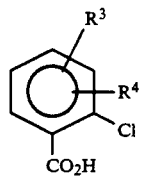

II may be mixed with an alkyl haloformate (e.g., ethyl chloroformate) under an inert atmosphere (e.g., argon) at about room temperature in an organic solvent (e.g., tetrahydrofuran) and treated with a base (e.g., triethylamine) and a reducing agent (e.g., sodium borohydride) to form alcohol

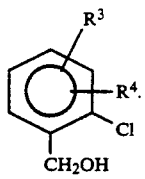

III

Compound III is reacted with a compound of the formula

IV wherein $R^{10}$ is acyl (e.g., acetyl) and Pro$^1$ is a silyl oxygen-protecting group such s tert-butyldimethylsilyl,

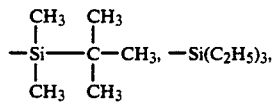

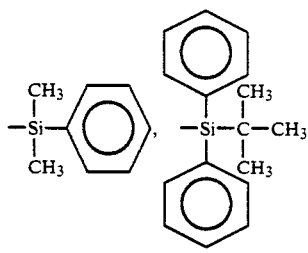

and the like. Compound IV maya be prepared by reacting a haolalcohol with a thioacid (e.g., thioacetic acid), followed by reaction with a silyl chloride (e.g., t-butyldimethylsilyl chloride) in an aorganic solvent (e.g., tetrahydrofuran) in the presence of a catalyst such as N-methylmorpholine.

Compounds III and IV are mixed in an organic solvent or solvent mixture (e.g., dimethylsulfoxide and methanol) at about 0° C. under an inert atmosphere (e.g., argon) and treated with a base such as sodium methoxide. The resulting product is oxidized by the method of Swern (Tetrahedron 34 (1978), 1651) to form an aldehyde

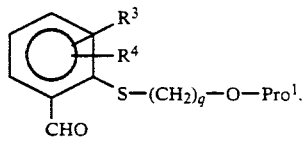

Alternatively, aldehyde V may be prepared from the known aldehyde

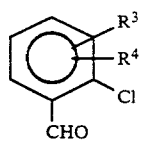

or from the known thiophenol

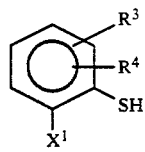

wherein $X^1$ is halo.

Aldehyde VI may be used instead of compound III and reacted with compound IV under the above conditions to form aldehyde V. Thiophenol VII reacts with a compound of the formula

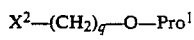

wherein $X^2$ is halo under the same conditions for reaction of compounds III and IV. The resulting product is metallated with an alkyl lithium (e.g., n-butyl lithium) in tetrahydrofuran at $-100°$, followed by addition of dimethylformamide to form aldehyde V.

Aldehyde V may be mixed with a compound of the formula

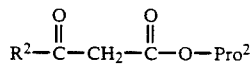

wherein $Pro^2$ is a sily oxygen-protecting group such as trimethylsilylethyl in an organic solvent (e.g., benzene), treated with reagents such as acetic acid and piperidine, and heated at about reflux temperature to form a compound of the formula

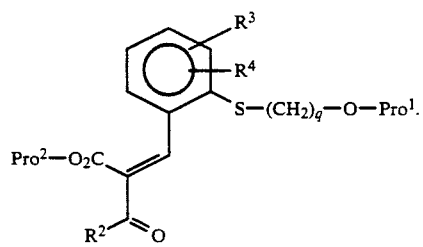

Compound IX may be prepared from diketene and a silylalcohol (e.g., trimethylsilylethanol) in an organic solvent (e.g., toluene) in the presence of a base (e.g., sodium acetate) at about 90° C.

Compound X is reacted with an alkylthiopseudourea of the formula

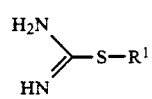

(e.g., 2-methylthiopseudourea hydrogen sulfate) by treatment in an inert organic solvent (e.g., dimethylformamide) under an inert atmosphere (e.g., argon) with a base (e.g., sodium acetate) at about room temperature, followed by heating to about 75° to form a compound of the formula

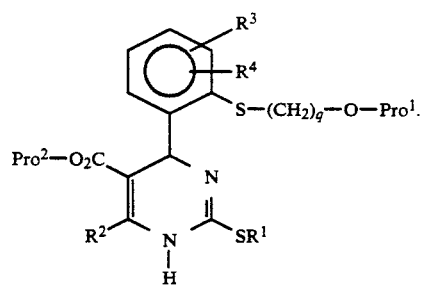

Compound XII is placed in an organic solvent (e.g., acetonitrile) under an inert atmosphere (e.g., argon) at about room temperature and is treated with a nitrogen-protecting agent (e.g., di-tert-butyldicarbonate), followed by a base (e.g., 4-(N,N-dimethylamino)pyridine) to form a compound of the formula

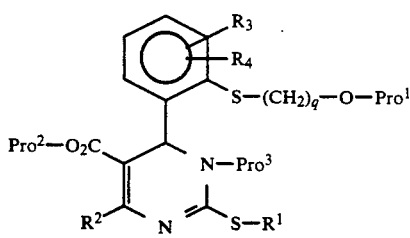

XIII wherein Pro³ is a nitrogen-protecting group (e.g., tert-butyoxycarbonyl).

Compound XIII is then oxygen-deprotected by treatment with a selective nucleophile (e.g., tetra-n-butylammonium fluoride) in an organic solvent (e.g., acetonitrile) under an inert atmoshphere (e.g., argon) at about 55° C. to form a compound of the formula

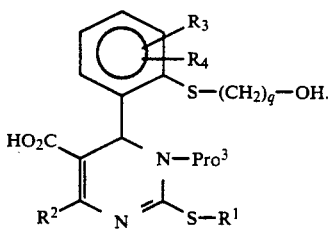

XIV

Compound XIV is then cyclized by a macrocyclic lactonization agent such as N-methyl-2-chloropyridinim iodide (see, for example, Mukaiyama et al., Chem. Lett. (1976), 49-50) in an inert solvent (e.g., acetonitrile) under an inert atmosphere (e.g., argon) in the presence of a base (e.g., triethylamine) at about 85° C. to form a compound of the formula

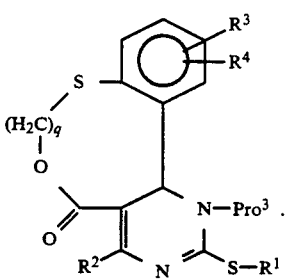

XV

Compound XV may be nitrogen-deprotected by, for example, a non-oxidizing acid (e.g., trifluoroacetic acid) in an organic solvent (e.g., methylene chloride) under an inert atmosphere (e.g., argon) at about 0° to 30° C. to form compound I.

The compounds of formula I have been represented structurally as 1,4-dihydropyrimidines. However, such structures are tautomeric and can also be structurally reoresented as 3,4-dihydropyrimidines, i.e.,

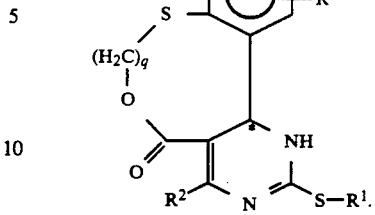

IA

Both forms are within the scope of this invention.

The compounds of formula I contain an asymmetric center within the dihydropyrimidine ring as represented by the *. Thus, the compounds of formula I can exist in enantiomeric forms or in mixtures thereof. R- amd S-isomers of compound I are separated by chromatography on a chiral HPLC column (e.g., Chiralcel OD, Diacel, Inc.).

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which R¹ or R² is

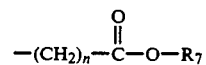

and R₇ is hydrogen include carboxylic acid salts, i.e., R₇ is a pharmaceutically acceptable salt-forming ion. Preferred salt-forming ions include alkali metal salt ions such as sodium, potassium, and lithium, and alkaline earth metal salt ions such as calcium and magnesium.

Use and Utility

The compounds of formula I and the pharmaceutically acceptable salts thereof are useful as cardiovascular agents.

Racemic mixtures of some compounds of formula I, such as Examples 2 and 3 herein, have shown both calcium agonist and antagonist activity. It is believed that R-isomers have antagonist activity and that S-isomers have agonist activity. Compounds of formula I, especially the R-isomers, act as calcium entry blocking vasodilators and are especially useful as antihypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg per kilogram of body weight per day, preferably from about 1 to about 50 mg per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as antiarrhythmic agents, as anti-asthmatic agents, and in limiting myocardial infarction.

The compounds of formula I can also be formulated in combination with a diuretic, or a beta-adrenergic agents, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril, fosinopril, and enalopril.

Some compounds of formula I, such as Examples 2 and 3 herein, have also shown calcium agonist activity. As a result of their calcium agonist activity, the compounds of formula I, especially the S-enantiomers, are useful in treating hypotension, congestive heart failure, shock and endocrinological disorders. A single dose (or preferably two to four divided daily doses) of about 0.1 to 100 mg per kilogram of body weight per day (preferably 1 to 50 mg/kg/day) is appropriate for these indications. The compound is preferably administered orally, but parenteral routes such as subcutaneous, intramuscular, or intravenous routes can also be employed.

The compounds of formula I can be formulated in compositions such as tablets, capsules or elixirs for oral administration, or in sterile solutions or suspensions for parenteral administration. About 10 to 500 mg, of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Specific Embodiments

The following working examples represent most preferred embodiments of this invention. All temperatures are in degrees Celsius. The preparation of intermediate compounds appears just below the names thereof. As a shorthand reference, the compound prepared in part 1-A shall be referred to as "compound 1-A" or "intermediate 1-A" and so forth for compounds prepared in parts 1-B, 1-C, 2-A, 2-B, etc.

EXAMPLE 1

3,8,9,10,11,16b-Hexahydro-4-methyl-2-(methylthio)-13-nitro-5H,7H-[7,1]benzoxathiacyclododecino[10,9-d]pyrimidin-5-one, monohydrochloride

1-A. 2-Chloro-3-nitrobenzyl alcohol

A mixture of 2-chloro-3-nitrobenzoic acid (2.01 g, 0.01 mol) and ethyl chloroformate (1.08 g, 0.01 mol) in 25 ml of dry tetrahydrofuran under argon at room temperature was treated with triethylamine (1.01 g, 0.01 mol) in 10 ml of tetrahydrofuran over a period of 15 minutes. After stirring for 1 hour, the solids were removed by filtration and the filtrate was treated dropwise with a solution of iodine borohydride (0.5 g, 0.013 mol) in 3 ml of water. Slight warming and copious gas evolution were noted. Solvent was removed in vacuo and the residue, dissolved in ethyl acetate, was washed with water, dilute sodium bicarbonate, water, 1N hydrochloric acid, water and saturated brine. The dried (magnesium sulfate) organic solution was concentrated in vacuo to give 1.69 g of crude solid product. Hexane trituration gave 1.5 g (80%) of product, melting point 67°–70°.

Analysis for $C_7H_6ClNO_3$:
Calc'd: C,44.82; H,3.23; N,7.47; Cl,18.90.
Found: C,44.96; H,3.12; N,7.15; Cl,18,73.

1-B. 3-Nitro-2-(5-tert-butyldimethylsilyloxy)pentylthiobenzaldehyde

A solution of compound 1-A (2.0 g, 10.1 mmol) and 1-acetylthio-5-tert-butyldimethylsilyloxypentane (3.2 g, 11.5 mmol, prepared from 5-chloropentan-1-ol by reaction with thioacetic acid, followed by tert-butyldimethylsily chloride) in 15 ml of dimethylsulfoxide:methanol (2:1) at 0° under argon was treated with 25% sodium methoxide/methanol (2.8 ml, 12.3 mmol). The reaction was stirred at room temperature for 1.5 hours, then diluted with ethyl acetate and washed with water, 1N sodium hydroxide, water and brine. The dried (anhydrous magnesium sulfate) organic solution was concentrated in vacuo and the residue was flash chromatographed on 600 ml of LPS-1 silica gel, eluting with ethyl acetate:hexane (1:4) to give 2.43 g (63%) of 3-nitro-2-(5-tert-butyldimethylsilyloxy)-pentylthiobenzyl alcohol.

Analysis for $C_{18}H_{35}NO_4SSi$:
Calc'd: C,55.48; H,9.05; N,3.60; S,8.23.
Found: C,56.19; H,8.38; N,3.64; S,8.34.

The alcohol (3.35 g, 8.7 mmol) obtained above was oxidized by the method of Swern (*Tetrahedron, 1978, 34, 1651*) to give 3.33 g (100%) of aldehyde 1-B (used in the next step without further purification).

Analysis for $C_{18}H_{33}NO_4SSi$:
Calc'd: C,56.34; H,7.62; N,3.65; S,8.36.
Found: C,56.30; H,7.80; N.3.42; S,8.44.

1-C. 2-(3-Nitro-2-(5-tert-butyldimethylsilyl oxy)-pentylthiophenylmethylene)-3-oxobutanoic acid, 2-(trimethylsilyl)ethyl ester A solution of compound 1-B (2.39 g, 6.2 mmol) and 3-oxobutanoic acid 2-(trimethylsilyl)ethyl ester (1.238 g, 6.8 mmol, prepared from diketene and trimethylsilylethanol in toluene containing sodium acetate at 90°, boiling point 60°–62°/0.3 mmHg) in 100 ml of benzene was treated with acetic acid (0.3 ml) and piperidine (0.3 ml) and heated at reflux temperature for 1 hour, using a Dean-Stark trap to collect formed water. The cooled mixture, diluted with ethyl acetate, was washed with 1N hydrochloric acid, water, dilute sodium bicarbonate and brine, dried (anhydrous magnesium sulfate) and concentrated in vacuo to give 3.75 g of amber oil. Flash chromatography on 400 ml of LPS-1 silica gel and elution with ethyl acetate/hexane (1:20) gave 2.92 g (82%) of product.

Analysis for $C_{27}H_{45}NO_6SSi_2 \cdot 0.2H_2O$:
Calc'd: C,56.75; H,8.01; N,2.45.
Found: C,56.58, H,8.16; N,2.69.

1-D 1,4-Dihydro-6-methyl-2-(methylthio)-4-(2-(5-tert-butyldimethylsilyloxypentylthio)-3-nitro-phenyl)-5-pyrimidinecarboxylic acid, 2-(trimethylsilyl)ethyl ester A solution of compound 1-C (2.9 g, 5.1 mmol) and 2-methylthiopseudourea hydrogen sulfate (0.75 g, 2.7 mmol) in 9 ml of dry dimethylformamide under argon at room temperature was treated with sodium acetate (0.44 g, 5.4 mmol) and heated at 75° for 4 hours. The cooled mixture, diluted with ethyl acetate, was washed with water and brine, dried (anhydrous magnesium sulfate) and concentrated in vacuo to give 3.75 g of an oil. Flash chromatography on 350 ml of LPS-1 silica gel and elution with ethyl acetate/hexane (1:6) gave 2.87 g (88%) of product as a pale viscous oil.

Analysis for $C_{29}H_{49}N_3O_5S_2Si_2$:
Calc'd C,54.52; H,7.72; N,6.53; S,10.02.
Found: C,54.65; H,7.94; N,6.29; S,9.46.

1-E
4-Methyl-2-(methylthio)-6-(2-(5-tert-butyldimethyl-silyloxypentylthio)-3-nitrophenyl)-1,5(6H)-pyrimidinedicarboxylic acid, 1-tert-butyl,5-(2-(trimethylsilyl)ethyl ester A solution of compound 1-D (2.78 g, 4.34 mmol) in 65 ml of acetonitrile under argon at room temperature was treated with di-tert-butyldicarbonate (1.13 g, 5.19 mmol), followed by 4-(N,N-dimethylamino)pyridine (65 mg, 0.52 mmol). After stirring for 2 hours, the mixture was diluted with ethyl acetate and washed with 1N hydrochloric acid, water, saturated sodium bicarbonate and brine. The dried (anhydrous magnesium sulfate) organic solution was concentrated in vacuo, and the residue (2.0 g) was flash chromatographed on 300 ml of LPS-1 silica gel, eluting with methylene chloride/hexane (2:1) to give 2.14 g (67%) of homogeneous oily product.

Analysis for $C_{34}H_{56}N_3O_7S_2Si_2$:
Calc'd: C, 55.17; H,7.76; N,5.68; S,8.66.
Found: C,55.33; H,8.12; N,5.36; S,8.45.

1-F.
1,4-Dihydro-6-methyl-2-(methylthio)-4-(2-(5-hydroxypentylthio)-3-nitrophenyl)-1,5(6H)-pyrimidinedicarboxylic acid,1-tert-butyl ester A solution of compound 1-E (1.90 g, 2.56 mmol) in 30 ml of acetonitrile containing tetra-n-butylammonium fluoride (10 ml of 1M tetrahydrofuran solution ) was stirred under argon at 55° for 2 hours. The reaction mixture, diluted with ethyl acetate, was washed with 1N hydrochloric acid, water (twice), and brine, then dried (anhydrous magnesium sulfate) and concentrated in vacuo to give 1.34 g of crude product. Flash chromatography on 250 ml of LPS-1 silica gel and elution with ethyl acetate/methanol (50:1) gave 1.03 g (76%) of product. Trituration with isopropylether/hexane gave an amorphous powder (contains some tetra-n-butyl ammonium salts; used in next step without further purification).

Analysis for $C_{23}H_{31}N_3O_7S_2$:
Calc'd C,52.55; H,5.95; N,7.99; S,12.20.
Found: C,53.96; „7.05; N,7.58; S,10.10.

1-G. 1-[(1,1-Dimethylethoxy)carbonyl]-1,8,9,10,11,16b-hexahydro-4-methyl-2-(methylthio)-13-nitro-5H,7H-[7,1]benzoxathiacyclododecino[10,9-d]pyrimidin-5-one To a solution of N-methyl-2-chloropyridinium iodide (1.4 g, 5.49 mmol) in 165 ml of dry acetonitrile under argon at 85° was added a mixture of compound 1-F (700 mg, 1.33 mmol) and triethylamine (1.68 ml, 1.22 g, 12.0 mmol) in 10 ml of acetonitrile via syringe pump over a period of 7 hours. After stirring an additional 0.5 hour at 85°, volatiles were stripped in vacuo and the residue, dissolved in ethyl acetate, was washed with 1N hydrochloric acid, water, saturated sodium bicarbonate and brine. The dried (anhydrous magnesium sulfate) organic solution was treated with Darco and concentrated to give 450 mg, which upon trituration with warm acetone gave 350 mg (52%) of product, melting point 176° d.

Analysis for $C_{23}H_{29}N_3O_6S_2$:
Calc'd: C,54.42; H,5.76; N,8.28; S,12.63.
Found: C,54.41; H,5.78; N,8.10; S,12.18.

1-H.
3,8,9,10,11,16b-hexahydro-4-methyl-2-(methylthio)-13-nitro-5H,7H-[7,1]benzoxathiacyclododecino[10,9-d]pyrimidin-5-one, monohydrochloride A solution of compound 1-G (300 mg, 0.59 mmol) in 1 ml of dichloromethane under argon at 0° C. was treated with 0.8 ml of trifluoroacetic acid and allowed to stir for several hours at room temperature. Volatiles were stripped in vacuo and the residue, dissolved in ethyl acetate, was washed with saturated sodium bicarbonate, water and brine. The dried (anhydrous magnesium sulfate) organic solution was concentrated and the residue triturated with hot acetone to give 233 mg (96%) of compound 1-H, melting point 271.5°–272.5°.

Analysis for $C_{18}H_{21}N_3O_4S_2$:
Calc'd: C,53.05; H,5.19; N,10.31; S,15.74 .
Found: C,52.23; H,5.14; N,9.98; S,15.74.

The above free base of compound 1-H (250 mg, 0.60 mmol), dissolved in 10 ml of dichloromethane/methanol (1:1) was treated with 0.5 ml of 4N ethereal hydrochloric acid. Volatiles were removed in vacuo and the residue triturated with hot acetonitrile, cooled and filtered to give 238 mg (88%) of the hydrochloric acid salt compound 1-H (Example 1), melting point>280°.

Analysis for $C_{18}H_{22}ClN_3S_2.0.25H_2O$:
Calc'd: C,48.20; H;5.05; N,9.37; S,14.02; Cl,7.90.
Found: C,48.21; H,4.83; N,9.27; S,14.30; Cl,8.04.

EXAMPLE 2
3,8,9,10,11,16b-Hexahydro-4-methyl-2-(methylthio)-15-nitro-5H,7H-[7,1]benzoxathiacyclododecino[10,9-d]pyrimidin-5-one, monohydrochloride

2-A.
5-Nitro-2-(5-tert-butyldimethylsilyloxy)-pentylthiobenzaldehyde

A solution of 2-chloro-5-nitrobenzaldehyde (1.5 g, 8.1 mmol) and 1-acetylthio-5-tert-butyldimethylsilyloxypentane (2.34 g, 8.5 mmol, prepared from 5-chloropentan-1-ol by reaction with thioacetic acid, followed by tert-butyldimethylsilyl chloride) in 18 ml of dimethylsulfoxide: methanol (1:1) at 0° under argon was treated with 25% sodium methoxide/methanol (2.1 ml, 9.3 mmol). The slightly exothermic reaction was stirred at room temperature for 1.5 hours, then diluted with ethyl acetate and washed with water and brine. The dried (anhydrous magnesium sulfate) organic solution was concentrated in vacuo and the residue was flash chromatographed on 600 ml of LPS-1 silica gel, eluting with ethyl acetate:hexane (1:7) to give 2.67 g (80%) of product.

Analysis for $C_{18}H_{33}NO_4SSi$:
Calc'd: C,56.34; H,7.62; N,3 65; S,8.36.
Found: C,56.31; H,7.67; N,3.75; S,8.48.

2-B
2-(5-Nitro-2-(5-tert-butyldimethylsilyloxy)-pentylthiophenylmethylene)-3-oxobutanoic acid, 2-(trimethylsilyl)ethyl ester A solution of compound 2-A (2.22 g, 5.8 mmol) and 3-oxobutanoic acid 2-(trimethylsilyl)ethyl ester (1.29 g, 6.4 mmol, prepared from diketene and trimethylsilylethanol in toluene containing sodium acetate at 90°, boiling point 60°-62°/0.3 mmHg) in 60 ml of benzene was treated with acetic acid (0.3 ml) and piperidine (0.3 ml) and heated at reflux temperature for 2 hours, using a Dean-Stark trap to collect formed water. The cooled mixture, diluted with ethyl acetate, was washed with 1N hydrochloric acid, water, dilute sodium bicarbonate and brine, dried (anhydrous magnesium sulfate) and concentrated in vacuo to give 3.61 g of amber oil. Flash chromatography on 1400 ml of LPS-1 silica gel and elution with methylene chloride/hexane (1:1, then 1, then 4:1) gave 2.78 g (78%) of product.

Analysis for $C_{27}H_{45}NO_6SSi_2$;
Calc'd: C,57.10; H,7.99; N,2.47; S,5.64.
Found: C,57.28; H,8.27; N,2.56; S,5.55.

2-C.
1,4-Dihydro-6-methyl-2-(methylthio)-4-(2-(5-tert-butyldimethylsilyloxypentylthio)-5-nitro-phenyl)-5-pyrimidinecarboxylic acid, 2-(trimethylsilyl)ethyl ester A solution of compound 2-B (2.6 g, 4.6 mmol) and 2-methylthiopseudourea hydrogen sulfate (0.67 g, 2.4 mmol) in 8 ml of dry dimethylformamide under argon at room temperature was treated with sodium acetate (0.39 g, 4.8 mmol) and heated at 75° for 4 hours. The cooled mixture, diluted with ethyl acetate, was washed with water and brine, dried (anhydrous magnesium sulfate) and concentrated in vacuo to give 3.1 g of an oil. Flash chromatography on 700 ml of LPS-1 silica gel and elution with ethyl acetate/hexane (1:6) gave 2.38 g (81%) of product as a pale viscous oil.

Analysis for $C_{29}H_{40}N_3O_5S_2Si_2$:
Calc'd C,54.42; H,7.72; N,6.53.
Found: C,54.41; H,7.71; N,6.34.

2-D. 2-D.
4-Methyl-2-(methylthio)-6-(2-(5-tertbutyldimethylsilyloxypentylthio)-5-nitrophenyl)-1,5(b 6H)-pyrimidinedicarboxylic acid, 1-tert-butyl,5-(2-(trimethylsilyl)ethyl ester A solution of compound 2-C (1.78 g, 2.78 mmol) in 40 ml of acetonitrile under argon at room temperature was treated with di-tert-butyldicarbonate (0.73 g, 3.33 mmol), followed by 4-(N,N-dimethylamino)pyridine (40 mg, 0.33 mmol). After stirring overnight and diluting with ethyl acetate, the mixture was washed with 10% potassium hydrogen sulfate, water, saturated sodium bicarbonate and brine. The dried (anhydrous magnesium sulfate) organic solution was concentrated in vacuo, and the residue (2.0 g) was flash chromatographed on 350 ml of LPS-1 silica gel, eluting with methylene chloride/hexane (1:2, then 1:1) to give 1.80 g (88%) of homogeneous oily product.

Analysis for $C_{34}H_{57}N_3O_7S_2Si_2$:
Calc'd C,55.17; H,7.76; N,5.68; S,8.66.
Found: C,55.10; H,7.83; N,5.62; S,8.69.

2-E.
1,4-Dihydro-6-methyl-2-(methylthio)-4-(2-(5-hydroxypentylthio)-5-nitrophenyl)-1,5(6H)-pyrimidinedicarboxylic acid, 1-tert-butyl ester A solution of compound 2-D (1.80 g, 2.43 mmol) in 20 ml of acetonitrile containing tetra-n-butylammonium fluoride (11 ml of 1M tetrahydrofuran solutin) was stirred under argon at 55° for 1.5 hours. The reaction mixture, diluted with ethyl acette, was washed with 10% potassium hydrogen sulfate, water (twice), and brine, then dried (anhydrous magnesium sulfate) and concentrated in vacuo to give 1.0 g of crude product. Flash chromatography on 300 ml of LPS-1 sillica gel and elution with ethyl acetate/methanol (50:1) gave 950 mg (70%) of product. A portion of this was triturated with isopropylether/hexane to give an amorphous powder, melting point 155° (contains some tetra-n-butyl ammonium; used in next step without further purification).

Analysis for $C_{23}H_{31}N_3O_7S_2$:
Calc'd C,52.55; H,5.95; N,7.99; S,12.20.
Found C,53.37; H,6.58; N,7.39; S,10.33.

2-F. 1-[(1,1-Dimethylethoxy)carbonyl]-1,8,9,10,11,16b-hexahydro-4-methyl-2-(methyl thio)-15-nitro-5H,7H-[7,1]benzoxathiacyclododecino[10,9-d]pvrimidin-5-one To a solution of N-methyl-2-chloropyridinium iodide (200 mg, 0.78 mmol) in 25 ml of dry acetonitrile under argon at 85° was added a mixture of compound 2-E (100 mg, 0.19 mmol) and triethylamine (240 μl, 174 mg, 1.7 mmol) in 4.5 ml of acetonitrile via syringe pump over a period of 7 hours. After stirring an additional 0.5 hours at 85°, volatiles were stripped in vacuo and the residue, dissolved in ethyl acetate, was washed with 1N hydrochloric acid, water, saturated sodium bicarbonate and brine. The dried (anhydrous magnesium sulfate) organic solution was treated with Darco and concentrated to give 88 mg, which upon trituration with warm acetone gave 65 mg (68%) product (6–7 mg, 6%) was recovered from the mother liquors by flash chromatography (ethyl acetate/hexane, 1:7).

Analysis for $C_{23}H_{29}N_3O_6S_2.0.5H_2O$:
Calc'd C,53.48; H,5.85; N,8.14; S,12.41.
Found: C,53.39; H,5.58; N,7.92; S,12.31.

2-G.
8,9,10,11,16b-Hexahydro-4-methyl-2-(methylthio)-15-nitro-5H,7H-[7,1]benzoxathiacyclododecino[10,9-d]pyrimidin-5-one, monohydrochloride A solution of compound 2-F (164 mg, 032 mmol) in 1 ml of dichloromethane under argon at 0° was treated with 0.5 ml of trifluoroacetic acid and allowed to stir for several hours at room temperature. Volatiles were stripped in vacuo and the residue, dissolved in ethyl acetate, was washed with saturated sodium bicarbonate, water and brine. The dried (anhydrous magnesium sulfate) organic solution was concentrated and the residue (150 mg) triturated with hexane containing a small amount of acetone to give 117 mg (89%) of the free base of compound 2-G, melting point 174°-176°.

Analysis for $C_{18}H_{21}N_3O_4S_2$:
Calc'd C,53.05; H,5.19; N,10.31; S,15.74.
Found: C,52.98; H,4.83; N,10.21; S,15.46.

The above free base (137 mg, 0.33 mmol), dissolved in 10 ml of dichloromethane/methanol (1:1) was treated with 0.3 ml of 4N ethereal hydrochloric acid. Volatiles were removed in vacuo and the residue triturated with hot acetonitrile, cooled and filtered to give 131 mg (88%) of the hydrochloric acid salt compound 2-G (Example 2), melting point 275° d.

Analysis for $C_{18}H_{22}ClN_3S_2 \cdot 0.3CH_3CN$:
Calc'd: C,48.96; H,5.06; N,10.13; S,14.05; Cl,7.77.
Found: C,49.08; H,5.27; N,9.90; S,13.82; Cl,7.43.

EXAMPLE 3

3,8,9,10,11,16b-Hexahydro-4-methyl-2-(methylthio)-5H,7H-[7,1]benzoxathiacyclododecino[10,9-d]pyrimidin-5-one, monohydrochloride

3-A.

2-(5-tert-Butyldimethylsilyloxy)-pentylthiobromobenzene

A solution of 2-bromothiophenol (3.78 g, 20.0 mmol) in acetone under argon at room temperature was treated with 1-chloro-5-tert-butyldimethylsilyloxypentane (5.0 g, 21.2 mmol, prepared from 5-chloropentan-1-ol and tertbutyldimethylsilyl chloride), followed by 1,8diazabicyclo[5,4,0]undec-7-ene (3.22 g, 21.2 mmol) and sodium iodide (300 mg, 2.0 mmol), and heated at reflux for 3 hours. Volatiles were removed in vacuo and the residue, dissolved in ethyl acetate, was washed with 1N hydrochloric acid water, 1N sodium hydroxide, water and brine. The dried (anhydrous magnesium sulfate) organic solution was concentrated to give 7.5 g. Flash chromatography on 1 L of LPS-1 silica gel and elution with ethyl acetate/hexane (1:40) gave 3.5 g (45%) of 2-(5-tert-butyldimethylsilyloxy)-pentylthiobromobenzene.

Analysis for $C_{17}H_{29}BrOSSi$:
Calc'd: C,52.42; H,7.51; Br,20.52; S,8.23.
Found C,52.57; H,7.59; Br,20.42; S,7.96.

3B. 3-B.

2-(5-tert-Butyldimethylsilyloxy)-pentylthiobenzaldehyde

A solution of compound 3-A (3.3 g, 8.5 mmol) in 30 ml of tetrahydrofuran/hexane (1:1) under argon at −100° was treated with n-butyl lithium (3.65 ml of 2.5M n-butyl lithium/hexane, 9.1 mmol) over 5 minutes. After an additional 10 minutes at −100°, dimethylformamide (1 ml) was added and the temperature allowed to return to ambient. A small amount of methanol was added to quench remaining n-butyl lithium and volatiles were removed in vacuo. The residue, dissolved in ethyl acetate, was washed with water, brine, dried (anhydrous magnesium sulfate) and concentrated to give 3.0 g approximately 100% of compound 3-B.

Analysis for $C_{18}H_{30}O_2SSi$:
Calc'd: C,63.85; H,8.93; S,9.47.
Found: C,63.66; H,9.14; S,9.55.

3-C.

2-2((5-tert-butyldimethylsilyloxy)pentylthiophenylmethylene)-3-oxobutanoic acid, 2-(trimethylsilyl)ethyl ester A solution of compound 3-B (3.0 g, 8.8 mmol) and 3-oxobutanoic acid 2-(trimethylsilyl)ethyl ester (1.79 g, 8.8 mmol, prepared from diketene and trimethylsilylethanol in toluene containing sodium acetate at 90°, boiling point 60°-62° /0.3 mmHg) in 50 ml of benzene was treated with acetic acid (0.3 ml) and piperidine (0.3 ml) and heated at reflux temperature for 2 hours, using a Dean-Stark trap to collect formed water. The cooled mixture, diluted with ethyl acetate, was washed with 1N hydrochloric acid, water, diluted sodium bicarbonate and brine, dried (anhydrous magnesium sulfate) and concentrated in vacuo to give 4.69 g of amber oil. Flash chromatography on 800 ml of LPS-1 gel and elution with ethyl acetate/hexane (1:20, then 1:10) gave 2.78 g (60%) of product.

Analysis for $C_{27}H_{45}NO_6SSi_2$:
Calc'd: C,62.02; H,8.87; S,6.13.
Found: C,62.13; H,9.05; S,6.14.

3-D.

1,4-Dihydro-6-methyl-2-(methylthio)-4-(2-(5-tert-butyldimethylsilyloxypentylthio)phenyl)5-pyrimidinecarboxylic acid, 2-(trimethylsilyl)ethyl ester A solution of compound 3-B (2.7 g, 5.17 mmol) and 2-methylthiopseudourea hydrogen sulfate (0.75 g, 2.71 mmol) in 10 ml of dry dimethylformamide under argon at room temperature was treated with sodium acetate (0.44 g, 5.4 mmol) and heated at 75° for 6 hours. The cooled mixture, diluted with ethyl acetate, was washed with water and brine, dried (anhydrous magnesium sulfate) and concentrated in vacuo to give 3.22 g of an oil. Flash chromatography on 600 ml of LPS-1 silica gel and elution with ethyl acetate/hexane (1:6) gave 2.30 g (75%) of product as a pale viscous oil.

Analysis for $C_{29}H_{50}N_2O_3S_2Si_2 \cdot 0.26H_2O$:
Calc'd: C,58.07; H,8.49; N,4.67; S,10.69.
Found: C,58.35; H,8.80; N,4.54; S,10.32.

3-E.

4-Methyl-2-(methythio)-6-(2-(5-tertbutyldimethylsilyloxypentylthio)phenyl)-1,5(6H)-pyrimidinedicarboxylic acid, 1-tert-buty1,5-(2-(trimethylsilyl)ethyl ester A solution of compound 3-D (2.25 g, 3.78 mmol) in 40 ml of acetonitrile under argon at room temperature was treated with di-tert-butyldicarbonate (0.98 g, 4.52 mmol), followed by 4-(N,N-dimethylamino)pyridine (55 mg, 0.45 mmol). After stirring for 1 hour and diluting with ethyl acetate, the mixture was washed with 10% potassium hydrogen sulfate, water, saturated sodium bicarbonate and brine. The dried (anhydrous magnesium sulfate) organic solution was concentrated in vacuo, and the residue (2.9 g) was flash chromatographed on 350 ml of LPS-1 silica gel, eluting with methylene chloride/hexane (2:1, then 3:1) to give 2.5 g (95%) of homogeneous oily product.

Analysis for $C_{34}H_{58}N_2O_5S_2Si_2$:
Calc'd C,58.74; H,8.41; N,4.03; S,9.22.
Found: C,58.72; H,8.74; N,3.93; S,9.53.

3-F.

1,4-Dihydro-6-methyl-2-(methylthio)-4-(2-(5-hydroxypentylthio)phenyl)-1,5(6H)-pyrimidinedicarboxylic acid, 1-tert-butyl ester A solution of compound 3-E (2.5 g, 3.6 mmol) in 35 ml of acetonitrile containing tetra-n-butylammonium fluoride (15 ml of 1M tetrahydrofuran solution) was stirred under argon at 55° for 4 hours. The reaction mixture was diluted with ethyl acetate, washed with 1N hydrochloric acid (three times), water (twice) and brine, dried with anhydrous magnesium sulfate, and concentrated in vacuo to give 1.56 g of product.

Analysis for $C_{23}H_{32}N_2O_5S_2 \cdot 0.29H_2O$:
Calc'd: C,56.85; H,6.76; N,5.77; S,13.20.
Found: C,57.01; H,6.87; N,5.61; S,12.81.

3-G. 1-Dimethylethoxy)carbonyl]-1,8,9,10,11,16b-hexahydro-4-methyl-2-(methylthio)-5H,7H-[7,1]benzoxathiacyclododecino[10,9-d]pyrimidin-5-one To a solution of N-methyl-2-chloropyridinium iodide (1.62 g, 6.36 mmol) in 40 ml of dry acetonitrile under argon at 85° was added a mixture of compound 3-F (746 mg, 1.55 mmol) and triethylamine (1.95 ml, 1.41 g, 14.0 mmol) in 9 ml of acetonitrile via syringe pump over a period of 8 hours. After stirring an addition 0.5 hour at 85°, volatiles were stripped in vacuo and the residue, dissolved in ethyl acetate, was washed with 1N hydrochloric acid, 10% potassium thiosulfate, water, saturated sodium bicarbonate and brine. The dried (anhydrous magnesium sulfate) organic solution was treated with Darco and concentrated to give 710 mg. Flash chromatography on 200 ml of LPS-1 silica gel and elution with ethyl acetate/hexane (1:14) gave 540 mg (75%) of solid product, melting point 150°–152°.

Analysis for $C_{23}H_{30}N_2O_4S_2$:
Calc'd: C,59.71; H,6.54; N,6.06; S,13.86.
Found: C,59.70; H,6.69; N,5.98; S,13.27.

3-H. 3,8,9,10,11,16b-hexahydro-4-methyl-2-(methylthio)-5H,7H-[7,1]benzoxathiacyclododecino[10,9-d]pyrimidin-5-one, monohydrochloride A solution of compound 3-G (420 mg, 0.91 mmol) in 2 ml of dichloromethane under argon at 0° C. was treated with 1 ml of trifluoroacetic acid and allowed to stir for 3 hours at room temperature. Volatiles were stripped in vacuo and the residue, dissolved in ethyl acetate, was washed with saturated soium bicarbonate, water and brine. The dried (anhydrous magnesium sulfate) organic solution was concentrated and the residue triturated with hexane containing a small amount of acetone to give 320 mg (97%) of the free base of compound 3-H, melting point 185°–187°.

Analysis for $C_{18}H_{22}N_2O_2S_2$:
Calc'd: C,59.64; H,6.12; N,7.73; S,17.69.
Found: C,59.81; H,6.29; N,7.50; S,17.10.

The above free base (220 mg, 0.60 mmol) was dissolved in 10 ml of dichloromethane/methanol (1:1) and treated with 0.4 ml of 4N ethereal hydrochloric acid. Volatiles were removed in vacuo and the residue triturated with hot acetonitrile, cooled and filtered to give 242 mg (100%) of the hydrochloric acid salt, compound 3-G (Example 3), melting point 271°–272°.

Analysis for $C_{18}H_{22}CN_3S_2.0.1H_2O$:
Calc'd: C,53.45; H;5.76; N,6.93; S,15.86; Cl,9.64.
Found: C,53.58; H,5.90; N,6.74; S,15.76; Cl,9.80.

EXAMPLES 4 to 8

Following the procedures of Example 1 using the starting material shown in column A, the followign additional formula I compounds may be prepared.

| Ex. A | g | $R^1$ | $R^2$ | $R^3$ | $R^4$ |
|---|---|---|---|---|---|
| 4. (2-NO$_2$, 3-Cl, CHO phenyl) | 4 | Me | Me | 13-NO$_2$ | H |
| 5. (4-O$_2$N, Cl, CHO phenyl) | 6 | Me | Me | 15-NO$_2$ | H |
| 6. (2,3-diCl, CHO phenyl) | 5 | Me | Me | 13-Cl | H |
| 7. (2-NO$_2$, 3-Cl, CHO phenyl) | 5 | CH$_2$—Ph | Me | 13-NO$_2$ | H |
| 8. (2-NO$_2$, 3-Cl, CHO phenyl) | 5 | Et | Et | 13-NO$_2$ | H |

Following the procedures of Example 3 using the starting material shown in column A, the following additional formula I compounds may be prepared.

| Ex. A | g | $R^1$ | $R^2$ | $R^3$ | $R^4$ |
|---|---|---|---|---|---|
| 9. (2-Br, SH phenyl) | 7 | Me | Me | H | H |
| 10. (2-Br, SH phenyl) | 7 | CH$_2$Ph | Me | H | H |
| 11. (2-Me, 3-Br, SH phenyl) | 5 | CH$_2$—Ph | Me | 13-Me | H |
| 12. (4-MeO, Br, SH phenyl) | 4 | Me | Me | 15-OMe | H |

"Me" refers to methyl; "Et" to ethyl; "Ph" to phenyl.

What is claimed is:
1. A compound of the formula

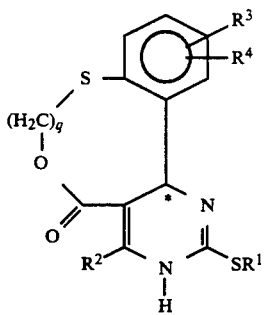

its 3,4-dihydropyrimidine tautomer form and pharmaceutically acceptable salts thereof, wherein:

$R^1$ is lower alkyl, lower alkenyl, lower alkynyl, —$(CH_2)_m$-cycloalkyl, —$(CH_2)_m$-aryl, —$(CH_2)_n$-heterocyclo, —$(CH_2)_p$—OH, —$(CH_2)_p$—O-lower alkyl, —$(CH_2)_p$—O—$(CH_2)_m$-aryl, —$(CH_2)_p$—SH, —$(CH_2)_p$—S-lower alkyl, —$(CH_2)_p$—S—$(CH_2)_m$-aryl,

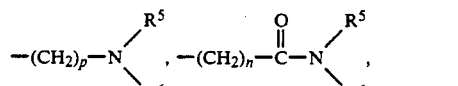

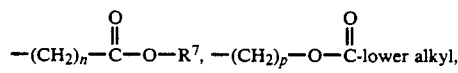

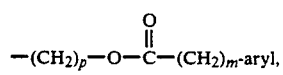

or halo substituted lower alkyl;

$R^2$ is hydrogen, lower alkyl, lower alkenyl, lower alkynyl, —$(CH_2)_m$-cycloalkyl, —$(CH_2)_m$-aryl, —$(CH_2)_n$-heterocyclo, —$(CH_2)_n$—OH, —$(CH_2)_n$—O-lower alkyl, —$(CH_2)_n$—O—$(CH_2)_m$-aryl, —$(CH_2)_n$—SH, —$(CH_2)_n$—S-lower alkyl, —$(CH_2)_n$—S—$(CH_2)_m$-aryl,

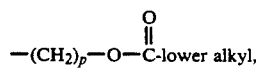

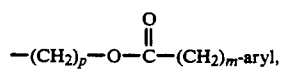

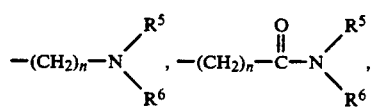

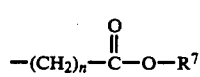

or halo substituted lower alkyl;

one of $R^3$ and $R^4$ is hydrogen and the other is lower alkyl of 1 to 4 carbons, lower alkylthio of 1 to 4 carbons, lower alkoxy of 1 to 4 carbons, halo, nitro, cyano, hydroxy, amino, —N—H-alkyl wherein alkyl is 1 to 4 carbons, —N(alkyl)$_2$ wherein alkyl is of 1 to 4 carbons, $CF_3$, NCS—, $OCHF_2$,

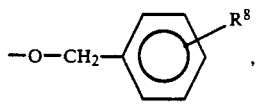

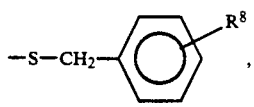

—O—$CH_2$-cycloalkyl, or —S—$CH_2$-cycloalkyl; or $R^3$ and $R^4$ are each independently methyl, methoxy, methylthio, halo, $CF_3$, nitro, amino, or $OCHF_2$;

$R^5$ and $R^6$ are independently selected from the group consisting of hydrogen, lower alkyl, and —$(CH_2)_m$-aryl or $R^5$ and $R^6$ together with the N atom to which they are attached complete a heterocyclic ring of the formula

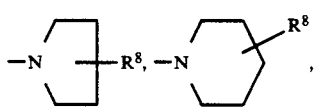

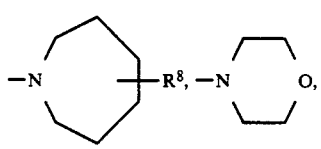

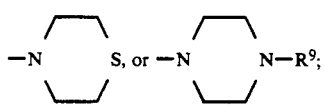

$R^7$ is hydrogen, lower alkyl, —$(CH_2)_m$-aryl, or a pharmaceutically acceptable salt forming ion;

$R^8$ is hydrogen, lower alkyl of 1 to 4 carbons, lower alkoxy of 1 to 4 carbons, lower alkylthio of 1 to 4 carbons, halo, hydroxy, or $CF_3$;

$R^9$ is hydrogen, lower alkyl of 1 to 4 carbons,

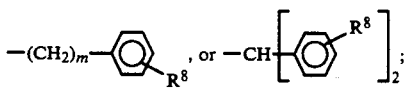

m is zero or an integer from 1 to 6;
n is an integer from 1 to 6;
p is an integer from 2 to 6; and
q is an integer from 3 to 8;
and wherein "heterocyclo" refers to 2- and 3-thienyl; 2- and 3-furyl; 2-, 3- and 4-pyridyl; imidazolyl; 4-, 5- 6-, and 7-indolyl; 4-5- 6-, and 7-isoindolyl; 5-, 6-, 7-, and 8- quinolinyl; 5-, 6-, 7-, and 8-isoquinolinyl; 4- 5-, 6- and 7-benzothiazolyl; 4-, 5-, 6-, and 7-benzoxazolyl; 4-, 5-, 6-, and 7-benzimidazolyl; 4-, 5-, 6-, and 7-benzoxadiazolyl; and 4-, 5-, 6-, and 7-benzofurazanyl.

2. The compound of claim 1, wherein $R^1$ is methyl.
3. The compound of claim 2, wherein $R^2$ is methyl.
4. The compound of claim 1, wherein one of $R^3$ and $R^4$ is hydrogen and the other is nitro.
5. The compound of claim 1, wherein q is 5.
6. The R-isomer of a compound of claim 1.
7. The S-isomer of a compound of claim 1.
8. The compounds of claim 1 having the names:

3,8,9,10,11,16b-Hexahydro-4-methyl-2-(methylthio)-13-nitro-5H,7H-[7,1]benzoxathiacyclododecino[10,9-d]pyrimidin-5-one, monohydrochloride, 3,8,9,10,11,16b-Hexahydro-4-methyl-2-(methylthio)-15-nitro-5H,7H-7,1]benzoxathiacyclododecinododecino[10,9-d]pyrimidin-5-one, monohydrochloride; and 3,8,9,10,11,16b-Hexahydro-4-methyl-2-(methylthio)-5H,7H-[7,1]benzoxathiacyclododecino [10,9-d]pyrimidin-5-one, monohydrochloride.

9. A method of reducing blood pressure in a mammal, which comprises administering to a hypertensive mammal an effective amount of a compound as defined in claim 1.

10. A composition useful in reducing blood pressure in a mammal, which comprises a pharmaceutically acceptable carrier and a antihypertensively effective amount of a compound as defined in claim 1.

* * * * *